(12) United States Patent
Boehm et al.

(10) Patent No.: US 7,145,010 B2
(45) Date of Patent: Dec. 5, 2006

(54) TERT-ALKYLPHENOXY-SUBSTITUTED POLYCYCLIC COMPOUNDS

(75) Inventors: Arno Boehm, Mannheim (DE); Willi Helfer, Friedelsheim (DE); Georg Beck, Boebingen (DE); Matthias Krieger, Mannheim (DE); Peter Erk, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 210 days.

(21) Appl. No.: 10/472,546

(22) PCT Filed: Mar. 20, 2002

(86) PCT No.: PCT/EP02/03279

§ 371 (c)(1),
(2), (4) Date: Sep. 23, 2003

(87) PCT Pub. No.: WO02/076988

PCT Pub. Date: Oct. 3, 2002

(65) Prior Publication Data

US 2004/0049030 A1     Mar. 11, 2004

Related U.S. Application Data

(60) Provisional application No. 60/278,009, filed on Mar. 23, 2001.

(51) Int. Cl.
*C07D 221/18*     (2006.01)
*D06P 1/00*     (2006.01)

(52) U.S. Cl. .............................. 546/26; 546/40; 8/636; 8/648

(58) Field of Classification Search .................. 546/26, 546/40; 8/636, 648
See application file for complete search history.

(56) References Cited

U.S. PATENT DOCUMENTS

| 5,986,099 | A * | 11/1999 | Mullen et al. ................. 546/26 |
| 6,737,159 | B1 * | 5/2004 | Garrett et al. ............... 428/332 |
| 2005/0222416 | A1 * | 10/2005 | Bohm et al. .................. 546/26 |

FOREIGN PATENT DOCUMENTS

| DE | 37 13 459 | 8/1988 |
| EP | 0 227 980 | 7/1987 |
| EP | 0 638 614 | 2/1995 |
| EP | 0 648 770 | 4/1995 |
| EP | 0 648 817 | 4/1995 |
| EP | 0 675 489 | 10/1995 |
| GB | 2 290 489 | 1/1996 |
| JP | 08 300814 | 11/1996 |
| WO | 96/22331 | 7/1996 |
| WO | 97/22607 | 6/1997 |
| WO | 98/32802 | 7/1998 |
| WO | 01 42331 | 6/2001 |

OTHER PUBLICATIONS

Holtrup et al., Chemistry, A European Journal, 1997, 3(2):219-225.*
Holtrup et al., 1997, CAS: 126:187360.*
J. Hofkens et al.: "Conformational rearrangements in and twisting of a single molecule" Chemical Physics Letters, vol. 333, No. 3,4, pp. 255-263 2001.
Huijun Xu et al.: "Aspects of metal pthalocyanine potosensitization systems for light energy conversion" Journal of Photochemistry and Photobiology, vol. 65, vol. 1-2, pp. 267-276 1992.
Frank Wurthner et al.: "Fluorescent and electroactive cyclic assemblies from perylene tetracarboxylic acid bismide ligands and metal phosphine triflates" Chemistry—A European Journal, vol. 7, No. 4, pp. 894-902, 2001.
C. Former et al.: "Cyclodehydrogenation of poly(perylene) to poly(quaterrylene): toward poly(pery-naphthalene)" MACROMOLECULES, vol. 35, No. 5, pp. 1576-1582 2000.
A. Herrmann et al.: "Polyphenylene dendrimers with perylene diimide as a luminescent core" Chemistry—A European Journal, vol. 7, No. 22, pp. 4844-4853 2001.

(Continued)

*Primary Examiner*—Kamal A. Saeed
*Assistant Examiner*—Robert Shiao
(74) *Attorney, Agent, or Firm*—Oblon, Spivak, McClelland, Maier & Neustadt, P.C.

(57) ABSTRACT

Tert-alkylphenoxy-substituted polycyclic compounds of the general formula I

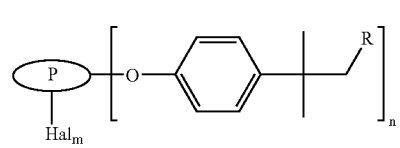

where
P is a conjugated polycyclic radical which is stable to bases and nucleophiles, optionally bears aryl substituents and contains no group from the group consisting of —CO—NH—CO—, —COOH and —CO—O—CO—;
R is $C_1$–$C_8$-alkyl, whose carbon chain may be interrupted by one or more groups selected from the group consisting of —O—, —S—, —$NR^1$—, —CO— and/or —$SO_2$— and which may be monosubstituted or polysubstituted by $C_1$–$C_6$-alkoxy or by a 5- to 7-membered heterocyclic radical which is attached via a nitrogen atom and may contain further heteroatoms and be aromatic; $C_5$–$C_8$-cycloalkyl whose carbon chain may be interrupted by one or more groups selected from the group consisting of —O—, —S—, —$NR^1$—, —CO— and/or —$SO_2$— and which may be monosubstituted or polysubstituted by $C_1$–$C_6$-alkyl;
$R^1$ is hydrogen or $C_1$–$C_6$-alkyl;
Hal is chlorine and/or bromine;
m is from 0 to 15;
n is from 1 to 16, subject to the proviso that the sum m+n is ≦16,
are prepared and used.

6 Claims, No Drawings

OTHER PUBLICATIONS

M. Koch et al.: "Reversibly crosslinked networks of nanoparticles in metallocene-catalyzed olefin polymerization" Macromoleuclar: Rapid Communications, vol. 22, No. 17, pp. 1455-1462 Dec. 11, 2001.

Frank Wurthner et al.: "Fluorescent J-type aggregates and thermotropic columnar mesophases of perylene bisimide dyes" Chemistry—A European Journal, vol. 7, No. 10, apges 2245-2253, 2001.

Adv. Mater., vol. 11, p. 754-758 1999.

Chem. Mater., vol. 12, pp. 352-362 2000.

* cited by examiner

TERT-ALKYLPHENOXY-SUBSTITUTED POLYCYCLIC COMPOUNDS

DESCRIPTION

The present invention relates to novel tert-alkyl-phenoxy-substituted polycyclic compounds of the general formula I

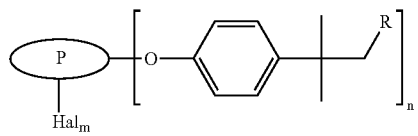

where
P is a conjugated polycyclic radical which is stable to bases and nucleophiles, optionally bears aryl substituents and contains no group from the group consisting of —CO—NH—CO—, —COOH and —CO—O—CO—;
R is $C_1$–$C_8$-alkyl, whose carbon chain may be interrupted by one or more groups selected from the group consisting of —O—, —S—, —NR$^1$—, —CO— and/or —SO$_2$— and which may be monosubstituted or polysubstituted by $C_1$–$C_6$-alkoxy or by a 5- to 7-membered heterocyclic radical which is attached via a nitrogen atom and may contain further heteroatoms and be aromatic; $C_5$–$C_8$-cycloalkyl whose carbon chain may be interrupted by one or more groups selected from the group consisting of —O—, —S—, —NR$^1$—, —CO— and/or —SO$_2$— and which may be monosubstituted or polysubstituted by $C_1$–$C_6$-alkyl;
$R^1$ is hydrogen or $C_1$–$C_6$-alkyl;
Hal is chlorine and/or bromine;
m is from 0 to 15;
n is from 1 to 16, subject to the proviso that the sum m+n is ≦16, and also to the preparation of these compounds and to their use for coloring high molecular weight organic and inorganic materials, as dispersing aids and pigment additives for organic pigments, as coloring component in decorative cosmetics and for preparing aqueous polymer dispersions that are colored or absorb in the ultraviolet and/or near infrared region of the electromagnetic spectrum.

Polycyclic organic compounds are frequently difficult to incorporate into application media because of poor solubility or compatibility. This problem arises particularly in the case of pigments, fluorescent dyes and UV absorbers where good dispersibility in the application medium is essential for, respectively, color strength, fluorescence and UV protection performance.

EP-A-648 817, EP-A-648 770 and WO-A-98/32802 describe the introduction of thermally redetachable alkoxycarbonyl substituents on the amino and imide nitrogen atoms for reversibly solubilizing, respectively, amino- and imino-containing chromophores. However, this method is limited to NH-containing chromophores and generally provides useful solubilization or compatibilization only in moderately polar media and only for low chromophore concentrations of <1% by weight. Moreover, the thermal fragmentation tendency of the carbamate function prevents use in high melting thermoplastics such as polymethyl methacrylate, polyethylene terephthalate and polycarbonate. Similarly the derivatization of diketopyrrolopyrroles with tertiary butyl groups that is described in DE-A-37 13 459 leads to the same limitations with regard to use levels and chromophore concentrations.

WO-A-96/22331, EP-A-227 980, WO-A-97/22607 and WO-A-96/22332 disclose perylene-3,4-dicarboxylic monoimides, perylene-3,4:9,10-tetracarboxylic diimides and quaterrylene-3,4:13,14-tetracarboxylic diimides that are substituted in the ring system by phenoxy radicals substituted by alkyl radicals containing up to 4 carbon atoms. These modified chromophores likewise have adequate solubility only in application media of medium polarity.

Adv. Mater. 11, 754–758 (1999) reports the formation of mesoscopic superstructures in organic solvents such as chloroform, carbon tetrachloride and methylcyclohexane by interaction of melamine bearing long-chain alkyl radicals with perylene- and N-(2-ethylhexyl)perylene-3,4:9,10-tetracarboxylic diimide having aryloxy substitution in the perylene structure. The poor solubility of the 1,6,7,12-tetraphenoxy-, -(p-tert-butyl)phenoxy- and -(p-tert-octyl)phenoxy-substituted perylene-3,4:9,10-tetracarboxylic diimides that are unsubstituted on the imide nitrogen is pointed out in this paper. The perylene derivatives described differ from the compounds of the invention in not being base-stable because of the unsubstituted nitrogen atom.

Chem. Mater., 12, 352–362 (2000) reports the incorporation into inorganic networks, via sol-gel processes, of perylene-3,4:9,10-tetracarboxylic diimides and perylene-3,4-dicarboxylic imides that are alkoxysilane-modified on the imide nitrogen atoms (and hence likewise not base-stable) and in some cases additionally aryloxy-substituted in the perylene structure. It is stated that the solubility of the perylene derivatives can be increased by the combination of a modification of the imide nitrogen atoms with a 3-triethoxysilylpropyl group and a substitution of the perylene structure by p-1,1,3,3-tetramethylbutylphenoxy groups.

It is an object of the present invention to provide novel polycyclic effect materials having distinctly improved solubility characteristics in both polar and nonpolar media (broadband compatibility) and a distinctly reduced tendency to aggregate.

We have found that this object is achieved by the tert-alkyl-phenoxy-substituted polycyclic compounds of the formula I defined at the beginning.

The invention also provides a process for preparing the compounds I, which comprises reacting a halide of the general formula II

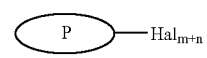

in an inert basic nitrogen-containing solvent in the presence of a base with a tert-alkylphenol of the general formula III

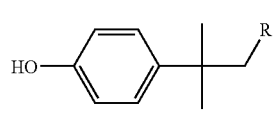

and if desired subsequently removing unwanted halogen.

The invention further provides for the use of the compounds I for coloring high molecular weight organic and inorganic materials, as dispersing aids and pigment additives for organic pigments, as coloring component in decorative cosmetics and also for preparing aqueous polymer dispersions that are colored or absorb in the ultraviolet and/or near infrared region of the electromagnetic spectrum.

The compounds of the formula I are based on a conjugated polycyclic radical P which is stable to bases and nucleophiles under the reaction conditions and contains no group from the group consisting of —CO—NH—CO—, —COOH and —CO—O—CO—.

P can bear further aryl substituents that are resistant to base attack, for example unsubstituted or alkyl- and/or alkoxy-substituted aryl, especially phenyl, or hetaryl, such as 2-, 3- and 4-pyridyl and pyrimidyl. These aryl substituents can either be attached directly to the ring structure or else, in the case of the hereinbelow recited polycyclic imides, to the imide nitrogen atoms.

The tert-alkylphenoxy radical(s) in such aryl-substituted P can also be attached to P via the aryl substituents, for example via the 4- or 3,5-positions of the phenyl radical in the case of diphenyldiketopyrrolopyrrole or N,N'-diphenylperylene-3,4:9,10-tetracarboxylic diimide.

Preferably P is a base-stable radical selected from the group consisting of naphthalenes, anthracenes, phenanthrenes, tetracenes, perylenes, terrylenes, quaterrylenes, pentarylenes, hexarylenes, anthraquinones, indanthrones, N-substituted naphthalene-1,8-dicarboxylic monoimides (hereinafter referred to as "naphthalmonoimides" for short), N,N'-disubstituted naphthalene-1,8:4,5-tetracarboxylic diimides ("naphthalimides" for short), N-substituted perylene-3,4-dicarboxylic monoimides ("perylmonoimides" for short), N,N'-disubstituted perylene-3,4:9,10-tetracarboxylic diimides ("perylimides" for short), N,N'-disubstituted terrylene-3,4:11,12-tetracarboxylic diimides ("terrylimides" for short), N,N'-disubstituted quaterrylene-3,4:13,14-tetracarboxylic diimides ("quaterrylimides" for short), acridines, carbazoles, dibenzofurans, dinaphthofurans, benzimidazoles, benzothiazoles, phenazines, dioxazines, quinacridones, metal phthalocyanines, metal naphthalocyanines, metal porphyrins, coumarins, dibenzofuranones, dinaphtho-furanones, benzimidazolones, indigo compounds, thioindigo compounds, quinophthalones, naphthoquinophthalones and diketopyrrolopyrroles.

Particular preference is given to P from the group consisting of naphthalenes, quinacridones, diketopyrrolopyrroles, dioxazines, indanthrones, metal phthalocyanines, metal naphthalocyanines, naphthalmonoimides, perylmonoimides, perylimides, terrylimides and quaterrylimides, and the metal phthalocyanines, metal naphthalocyanines, metal porphyrins, terrylimides and quaterrylimides are very particularly preferred.

The tert-alkylphenoxy radicals characterizing the compounds I and also any halogen atoms present in addition may be attached directly or, as described above, via any aryl substituents to the ring structure of P. It will be appreciated that both forms of attachment can occur in one and the same compound I. Relatively large P moieties, such as perylmonoimides, perylimides, terrylimides and quaterrylimides, bear the tert-alkylphenoxy radicals preferably directly on the ring structure or have at least directly attached tert-alkylphenoxy radicals in addition to arylene-attached tert-alkylphenoxy radicals.

Depending on the size of the conjugated ring system, the compounds I contain from at least 1 to 16 (n: 1–16), especially from 2 to 8, tert-alkylphenoxy radicals.

The process of the invention introduces the tert-alkylphenoxy radicals into the compounds I by replacement of halogen. Accordingly, if not all the halogen atoms are replaced, the compounds I can also contain up to 15 (m: 0–15), especially from 1 to 4, halogen atoms, in which case the total number of the two substituent groups should not exceed 16, preferably 8.

Generally suitable and preferred ranges for m+n will now be mentioned by way of example for particularly preferred P: naphthalenes: 1–4, especially 1–2; quinacridones: 1–8, especially 2–4; diketopyrrolopyrroles: 1–6, especially 2–4; dioxazines: 1–8, especially 2–4; indanthrones: 1–6, especially 2–4; metal phthalocyanines: 1–16, especially 4–8; metal naphthalocyanines: 1–16, especially 8–16; naphthalmonoimides: 1–4, especially 1–2; perylmonoimides: 1–6, especially 1–3; perylimides: 1–8, especially 2–6; terrylimides: 1–12, especially 2–8; quaterrylimides: 1–14, especially 2–8.

When P contains additional aryl substituents not used for attaching tert-alkylphenoxy, the maximum for the sum m+n decreases accordingly, of course.

Suitable examples of the R and $R^1$ radicals appearing in the formula I and also of their substituents will now be recited:

methyl, ethyl, propyl, isopropyl, butyl, isobutyl, tert-butyl, pentyl, isopentyl, neopentyl, tert-pentyl, hexyl, 2-methylpentyl, tert-pentyl, hexyl, 2-methylpentyl, heptyl, 1-ethylpentyl, octyl, 2-ethylhexyl and isooctyl;

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxy-butyl, 2- and 4-ethoxybutyl, 2- and 4-propoxybutyl, 3,6-dioxa-heptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl and 3,6,9-trioxaundecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithia-nonyl, 4,7-dithiaoctyl, 4,7-dithianonyl, 2- and 4-butylthiobutyl, 4,8-dithiadecyl, 3,6,9-trithiadecyl and 3,6,9-trithiaundecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-monomethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl and 3,6,9-trimethyl-3,6,9-triazaundecyl;

propan-2-on-1-yl, butan-3-on-1-yl, butan-3-on-2-yl and 2-ethyl-pentan-3-on-1-yl;

2-methylsulfonylethyl, 2-ethylsulfonylethyl, 2-propyl-sulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclo-octyl, 2-, 3-, 4- and 5-methylcyclooctyl, 2-, 3-, 4- and 5-ethylcyclooctyl, 3-, 4- and 5-propylcyclooctyl, 2-dioxanyl, 4-morpholinyl, 2- and 3-tetrahydrofuryl, 1-, 2- and 3-pyrrolidinyl and 1-, 2-, 3- and 4-piperidyl.

Examples of preferred tert-alkoxyphenoxy radicals are p-(1,1-dimethylpropyl)phenoxy, p-(1,1-dimethylbutyl)phenoxy, p-(1,1-dimethylpentyl)phenoxy, p-(1,1,3,3-tetra-methylbutyl)phenoxy, p-(2-cyclopentyl-1,1-dimethylethyl)phenoxy, p-(2-cyclohexyl-1,1-dimethylethyl)phenoxy, p-(2-cycloheptyl-1,1-dimethylethyl)phenoxy and p-(1,1-dimethyl-2-(4-morpholinyl)-ethyl)phenoxy.

The particularly preferred naphthalmonoimides, perylmonoimides, perylimides, terrylimides and quaterrylimides bear in particular the following base-stable substituents on the imide nitrogen atoms:

$C_6$–$C_{30}$-alkyl whose carbon chain may be interrupted by one or more groups selected from the group consisting of —O—, —S—, —NR$^1$—, —CO— and/or —SO$_2$— and which may be monosubstituted or polysubstituted by $C_1$–$C_6$-alkoxy or by a 5- to 7-membered heterocyclic radical which is attached via a nitrogen atom and may contain further heteroatoms and be aromatic;

$C_5$–$C_8$-cycloalkyl whose carbon chain may be interrupted by one or more groups selected from the group consisting of —O—, —S—, —NR$^1$—, —CO— and/or —SO$_2$— and which may be monosubstituted or polysubstituted by $C_1$–$C_6$-alkyl;

aryl or hetaryl which may each be monosubstituted or polysubstituted by $C_1$–$C_{18}$-alkyl, $C_1$–$C_6$-alkoxy, cyano, —CONH—R$^1$ and/or —NH—COR$^1$.

The following radicals may be specifically mentioned by way of example for these substituents in addition to the radicals already mentioned:

nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the designations, isononyl, isodecyl and isotridecyl as well as the above-mentioned designation isooctyl are trivial names derived from the alcohols obtained by the oxo process);

3,6,9-trioxadodecyl, 3,6,9,12-tetraoxatridecyl and 3,6,9,12-tetraoxatetradecyl; 3,6,9-trithiadodecyl, 3,6,9,12-tetrathiatridecyl and 3,6,9,12-tetrathiatetradecyl;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl and decylaminocarbonyl; formylamino, acetylamino and propionylamino;

2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl and 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl; 3- and 4-carboxamidophenyl, 3- and 4-N-(methyl)carboxamidophenyl and 3- and 4-N-(ethyl)carboxamidophenyl; 3- and 4-acetylaminophenyl, 3- and 4-propionylaminophenyl and 3- and 4-butyrylaminophenyl.

The inventive compounds I are advantageously preparable by the similarly inventive process by reacting the corresponding halides of the formula II with tert-alkylphenols of the formula III in an inert basic nitrogen-containing solvent in the presence of a base and if desired subsequently removing unwanted halogen.

Useful inert basic nitrogen-containing solvents are in particular polar solvents, especially nitrogen-containing heterocycles, such as pyridine, pyrimidine, quinoline, isoquinoline, quinaldine and preferably N-methylpyrrolidone, and also carboxamides, such as N,N-dimethylformamide and N,N-dimethylacetamide.

The solvent quantity depends on the solubility of the halide II and is customarily in the range from 2 to 40 g, preferably from 4 to 25 g, of solvent per g of halide II.

Useful bases are in particular nonnucleophilic or only weakly nucleophilic compounds. Examples of such bases are alkali metal hydroxides, such as potassium hydroxide and sodium hydroxide, alkali metal carbonates, such as potassium carbonate and sodium carbonate, and also alkali metal alkoxides of tertiary alcohols, such as lithium tert-butoxide, sodium tert-butoxide and potassium tert-butoxide, which are used in anhydrous form.

In general, from 0.8 to 1.5, preferably from 1.0 to 1.2, mol equivalents of base are used per mole of halogen atom to be replaced.

The halides II used as starting materials are generally known or obtainable according to known methods by reacting the unhalogenated conjugated polycyclic compounds with halogenating agents, especially the elemental halogens. Such halides II that contain halogen atoms attached to aryl substituents are known to be generally obtainable by introduction of the halogenated aryl radicals into the polycyclic system.

The molar ratio of halide II to phenol III depends on the number of halogen atoms to be replaced. In general, from 1 to 2, preferably from 1 to 1.3, mol of phenol III is used per mole of halogen atom to be replaced in halide II.

The reaction temperature is customarily in the range from 50 to 200° C., preferably at from 60 to 140° C.

It is advisable for the reaction to be carried out under protective gas, for example nitrogen or argon.

The reaction time depends on the reactivity of the halide II and is about 2–48 h.

Varying the reaction conditions—amount of phenol III and base and the reaction temperature—advantageously provides control over the halogen replacement, so that it is no problem to prepare not only products I where all the halogen atoms have been replaced (m=0) but also products I which do contain halogen. If desired, the halogen can subsequently be removed from the product I. Thus, a single starting material II can be used, if desired, to prepare various products I.

The process is advantageously carried out by initially charging the solvent, adding halide II, phenol III and base and heating the resulting solution or suspension to the desired reaction temperature for 2–48 h while stirring under protective gas.

After cooling down to room temperature, the reaction product can be isolated by filtering off the precipitated reaction product directly or after dilution with 3 to 4 times the volume of water, a dilute inorganic acid, for example 5–10% by weight hydrochloric acid, or an aliphatic alcohol, for example methanol, washing first with a little solvent and then with water to neutral run-off and drying under reduced pressure.

In some cases, especially when the bromides II, which are more base-labile and hence more prone to undesirable secondary reactions, are to be used to provide high degrees of substitution n, it can be advantageous, for achieving high product purity, for the phenoxylation reaction to be carried out in two stages. In this case, the halide II is initially reacted with only a portion, advantageously the amount needed to replace the most labile halogen substituents, of phenol III and base, the partially phenoxylated product is separated from the reaction mixture by filtration and is subsequently reacted with the rest of phenol III and base to form the desired product.

In general, the compounds I obtained according to the invention have a sufficiently high assay (>95%) that there is no need for further purification. Analytically pure products can be prepared by recrystallization from aromatic solvents, such as toluene and xylene, or halogenated hydrocarbons, such as methylene chloride and chloroform, or by filtration of a solution of the products in these solvents through silica gel and subsequent concentrating.

If only part of the halogen substituents was replaced and the halogen atoms still present are to be removed, this can be done by means of known methods.

By way of example, two dehalogenations will now be described which would be very advantageous for this purpose.

In the first method, the dehalogenation is base-induced in the presence of an inert basic nitrogen-containing or aromatic solvent.

Useful bases for this purpos include for example alkali metal hydroxides, such as potassium hydroxide and sodium hydroxide, alkali metal carbonates, such as potassium carbonate and sodium carbonate, alkali metal alkoxides of secondary and tertiary alcohols such as lithium isopropoxide, sodium isopropoxide, potassium isopropoxide, lithium tert-butoxide, sodium tert-butoxide and potassium tert-butoxide, and also sterically hindered nitrogen bases, such as diazabicyclooctane (DABCO), diazabicyclononene (DBN) and diazabicycloundecene (DBU).

The amount of base is not critical as such. It is customary to use from 1 to 3, preferably from 1 to 1.5, mol equivalents of base per mole of halogen atom to be eliminated.

Useful solvents include not only aromatic solvents, such as toluene and xylene, but also the same solvents as used in the phenoxylation, the use level of which in turn depends on the solubility of the compound I to be dehalogenated and is generally in the range from 2 to 50 g, preferably in the range from 5 to 25 g, per g of compound I.

The reaction temperature is customarily in the range from 50 to 200° C., preferably at from 60 to 130° C.

It is advisable for the dehalogenation to be carried out under protective gas, for example nitrogen or argon.

The reaction time depends on the reactivity of the compound I to be dehalogenated and is about 1–6 h.

The process is advantageously carried out by initially charging a solution or suspension in the solvent of the compound I to be dehalogenated, adding the base and heating the resulting mixture to the desired reaction temperature for 1–6 h while stirring under protective gas. When there is a risk of undesirable secondary reactions, for example saponifications, it is advantageous for the base not to be added until after the heating to reaction temperature.

After cooling down to room temperature, the reaction product can be isolated by diluting the reaction mixture with from 3 to 4 times the volume of a dilute inorganic acid, for example 5–10% by weight hydrochloric acid, filtering off the thusly precipitated product, washing initially with the dilute acid and then with methanol or water to neutral run-off and drying under reduced pressure.

The second method comprises a transition metal catalyzed reductive dehalogenation in the presence of a solvent that is inert under the reaction conditions.

The reducing agents used here are preferably complex hydrides, especially aluminohydrides, such as lithium aluminohydride, and especially borohydrides, preferably sodium borohydride, or elemental hydrogen.

The amount of reducing agent is not critical as such. Generally from 1 to 5, preferably from 2 to 3, mol equivalents of reducing agent are used per mole of halogen atom to be eliminated.

Useful transition metal catalysts include in particular palladium compounds, such as Pd(II) and Pd(0) compounds. The reduction with complex hydrides is preferably catalyzed using palladium(II) acetate, dichloro(1,5-cyclooctadiene)palladium(II), dichloro[1,1'-bis(diphenylphosphino)ferrocene]palladium(II), tris(dibenzylideneacetone)dipalladium(0), tetrakis(triphenyl-phosphine)palladium(0) and tetrakis(tris-o-tolylphosphine)-palladium(0) and the reduction with elemental hydrogen is preferably catalyzed using palladium-doped activated carbon.

Generally from 0.5 to 2 mol % of catalyst are used per mole of halogen atom to be eliminated.

The choice of solvent depends on the choice of reducing agent. When complex hydrides are used, it is especially polar aprotic solvents, such as aliphatic and cycloaliphatic ethers, aromatic solvents and aliphatic nitriles, which are suitable, while it is especially aliphatic alcohols which are suitable if elemental hydrogen is used.

Specific examples of these solvents are diethyl ether, tetrahydrofuran and dioxane, toluene and xylene, acetonitrile, which is used with borohydrides in particular, and also methanol and ethanol.

The amount of solvent is determined by the solubility of the compound I to be dehalogenated and is generally in the range from 2 to 50 g, preferably in the range from 5 to 25 g, per g of compound I.

The reaction temperature is customarily in the range from 0 to 150° C., preferably in the range from 20 to 100° C., although the reduction with complex hydrides is generally carried out at higher temperatures (about 50–100° C.) than the reduction with elemental hydrogen.

When complex hydrides are used as reducing agents, it is advisable to work under protective gas. A hydrogenation with elemental hydrogen is advantageously performed under a small hydrogen overpressure.

Depending on the reactivity of compound I, the dehalogenation takes from 4 to 72 h.

The process for dehalogenating with complex hydrides is advantageously carried out by initially charging the solvent, adding the compound I to be dehalogenated and the hydride, and heating the resulting solution or suspension to the desired reaction temperature for 4–72 h while stirring under protective gas.

After cooling down to room temperature and destroying excess hydride by addition of water, the reaction product can be isolated as described for the base-induced dehalogenation.

The process for dehalogenating with elemental hydrogen is advantageously carried out by initially charging a hydrogenation reactor with a suspension, in the solvent, of the compound I to be dehalogenated and the catalyst and heating to the reaction temperature for 4–72 h while stirring under a small hydrogen overpressure (about 0.1–0.5 bar).

After cooling down to room temperature, depressurizing and displacing excess hydrogen with nitrogen, the reaction product can be isolated as already described.

To produce compounds I having a >95% assay, the as-dehalogenated compounds can be subjected to a purification step. Useful purification options include for example fractional crystallization from solvent mixtures with an aromatic solvent, such as toluene and xylene, or a halogenated hydrocarbon, such as methylene chloride, chloroform and 1,1,2,2-tetrachloroethane, as one component and an extremely nonpolar solvent, such as pentane or hexane, as the other component or column chromatography over silica gel using these solvent mixtures as mobile phase.

The compounds I according to the invention are notable for their high solubility in, ie. their very good compatibility with, not only polar media (eg. aliphatic alcohols and esters on the one hand and polyacrylates, polycarbonates and polyesters on the other) but also nonpolar media (respectively alkanes and polyolefins, for example).

They may be used with advantage for a multiplicity of applications, for example for coloring or additivating high molecular weight organic and inorganic materials, especially plastics, paints and printing inks, and oxidic materials, such as low temperature ceramics and pigments based on metal oxides, specifically multilayer interference pigments containing metal oxides as individual layers, as dispersing aids and pigment additive for organic pigments, as coloring component in decorative cosmetics and also for preparing aqueous polymer dispersions that are colored or absorb in the UV and/or NIR, in which case the process described in WO-A-99/40123 may be employed in particular.

Applications where a compound I is desired that is colored, ie. that absorbs in the visible region of the electromagnetic spectrum, are usefully implemented using in particular such compounds I as contain a P from the group consisting of perylenes, terrylenes, quaterrylenes, pentarylenes, hexarylenes, indanthrones, perylmonoimides, perylimides, terrylimides, dinaphthofurans, dioxazines, quinacridones, metal phthalocyanines, metal porphyrins, coumarins, dinaphthofuranones, indigo compounds, thioindigo compounds, quinophthalones, naphthoquinophthalones and diketopyrrolopyrroles.

Applications requiring a compound I that is colorless or only weakly colored, absorbing in the ultraviolet and/or near infrared region of the electromagnetic spectrum, for example additivating high molecular weight organic and inorganic materials, as dispersing aids for organic pigments and also for preparing aqueous polymer dispersions that absorb in the UV and/or NIR, are usefully implemented using in particular such compounds I as contain a P from the group consisting of naphthalenes, anthracenes, phenanthrenes, tetracenes, anthraquinones, naphthalmonoimides, naphthalimides, quaterrylimides, acridines, carbazoles, dibenzofurans, benzimidazoles, benzothiazoles, phenazines, metal naphthalocyanines, dibenzofuranones and benzimidazolones.

Useful pigment additives for organic pigments include not only the colorless or only weakly colored compounds I, but also colored compounds I whose self-color is substantially coincident with the self-color of the pigments to be additivated.

EXAMPLES

A) Preparation of Compounds I According to the Invention

Examples 1 to 9

A mixture of x g (20 mmol) of halide II, y g of tert-alkylphenol III, z g of base B and a ml of N-methylpyrrolidone was heated to T° C. for t h while stirring in a nitrogen atmosphere.

After cooling down to room temperature, the precipitated reaction product was filtered off either directly (Example 6) or after dilution with three times the volume of methanol (Examples 1 to 3), water (Example 8) or 5% by weight hydrochloric acid (Examples 4, 5, 7 and 9) and washed with water to neutral run-off. In the case of Examples 1 to 3 on the one hand and 6 on the other, the filter residue was previously washed with, respectively, a little methanol or a little N-methylpyrrolidone. In the case of Examples 6 and 7 a column filtration with methylene chloride as mobile phase was additionally carried out. The final drying was carried out in all cases at 100° C. under reduced pressure.

This reaction led in all examples to the complete replacement of the halogen atoms by the tert-alkylphenoxy radicals.

Further details concerning these experiments and their results are summarized in Table 1. The yield in g is the total yield, while the yield in % is based on the desired phenoxylation product.

Table 1 uses the following designations:

TABLE 1

| Ex. | x [g] | Hal. II | y [g] | Alkylphenol III | z [g] | Base B | a [ml] | t [h] | T [° C.] | Yield [g]/[%] | Appearance |
|---|---|---|---|---|---|---|---|---|---|---|---|
| 1 | 14.4 | IIa | 13.6 | p-t-octylphenol | 4.55 | potassium carbonate | 150 | 6 | 90 | 18.8/–* | dark red, microcrystalline |
| 2 | 17.0 | IIb | 21.5 | p-t-octylphenol | 6.1 | potassium carbonate | 150 | 15 | 90 | 22.0/72 | deep red, microcrystalline |
| 3 | 17.0 | IIb | 24.2 | p-(2-cyclohexyl-1,1-dimethyl-ethyl)phenol | 6.1 | potassium carbonate | 150 | 12 | 90 | 24.8/76 | dark red, crystalline |
| 4 | 17.4 | IIc | 9.1 | p-t-octylphenol | 3.3 | potassium carbonate | 175 | 15 | 100 | 19.7/88 | dark red, crystalline |

TABLE 1-continued

| Ex. | x [g] | Hal. II | y [g] | Alkylphenol III | z [g] | Base B | a [ml] | t [h] | T [° C.] | Yield [g]/[%] | Appearance |
|---|---|---|---|---|---|---|---|---|---|---|---|
| 5 | 17.7 | IId | 9.1 | p-t-octylphenol | 3.3 | potassium carbonate | 200 | 15 | 100 | 18.6/82 | brownish red, microcrystalline |
| 6 | 28.6 | IIe | 32.2 | p-t-octylphenol | 9.95 | potassium carbonate | 150 | 10 | 95 | 31.0/71** | light green, amorphous |
| 7 | 28.6 | IIe | 32.2 | p-t-octylphenol | 13.5 | potassium t-butoxide | 200 | 4 | 80 | 28.0/64** | light green, amorphous |
| 8 | 10.2 | IIf | 10.3 | p-t-octylphenol | 3.05 | potassium carbonate | 250 | 48 | 100 | 5.6/74*** | bluish green, microcrystalline |
| 9 | 10.0 | IIg | 30.0 | p-t-octylphenol | 7.0 | potassium carbonate | 100 | 48 | 140 | 8.4/64 | bluish green, amorphous |

*Isomeric mixture of tri-, mono- and di-(p-tert-octyl)phenoxylated product
**1:1 mixture of N,N'-bis(2,6-diisopropylphenyl)-1,6,8,11,16,18-hexa(p-tert-octylphenoxy)-quaterrylene-3,4:13,14-tetracarboxylic diimide and N,N'-bis(2,6-diisopropyl-phenyl)-1,6,8,11,16,19-hexa(p-tert-octylphenoxy)quaterrylene-3,4:13,14-tetracarboxylic diimide
***Yield based on tetrachloroindanthrone fraction in IIf
IIa: N-(2,6-diisopropylphenyl)-1,6,9-tribromoperylene-3,4-dicarb-oximide (84% pure; additionally contains mono- and dibrominated N-(2,6-diisopropylphenyl)perylene-3,4-dicarboximide
IIb: N,N'-bis(2,6-diisopropylphenyl)-1,6,7,12-tetrachloroperylene-3,4:9,10-tetracarboxylic diimide
IIc: N,N'-bis(2,6-diisopropylphenyl)-1,7-dibromoperylene-3,4:9,10-tetracarboxylic diimide
IId: N,N'-didodecyl-1,7-dibromoperylene-3,4:9,10-tetracarboxylic diimide
IIe: 1:1 mixture of N,N'-bis(2,6-diisopropylphenyl)-1,6,8,11,16,18-hexabromoquaterrylene-3,4:13,14-tetra-carboxylic diimide and N,N'-bis(2,6-diisopropylphenyl)-1,6,8,11,16,19-hexabromoquaterrylene-3,4:13,14-tetra-carboxylic diimide
IIf: chlorinated indanthrone having an average degree of chlorination of 2 and containing 30% by weight of tetra-chloroindanthrone
IIg: chlorinated copper phthalocyanine having an average degree of chlorination of 3 (chlorine content 15.6% by weight)

Example 10

Example 6 was repeated to react 28.6 g of a 1:1 mixture of N,N'-bis(2,6-diisopropylphenyl)-1,6,8,11,16,18-hexabromo-quaterrylene-3,4:13,14-tetracarboxylic diimide and N,N'-bis(2,6-diisopropylphenyl)-1,6,8,11,16,19-hexabromo-quaterrylene-3,4:13,14-tetracarboxylic diimide with 20.6 g of p-tert-octylphenol and 6.9 g of potassium carbonate.

This afforded 27.6 g of a 1:1 mixture of N,N'-bis(2,6-diiso-propylphenyl)-8,18-dibromo-1,6,11,16-tetra(p-tert-octylphenoxy)-quaterrylene-3,4:13,14-tetracarboxylic diimide and N,N'-bis(2,6-diisopropylphenyl)-8,19-dibromo-1,6,11,16-tetra(p-tert-octylphenoxy)quaterrylene-3,4:13,14-tetra-carboxylic diimide in the form of a dark green crystalline powder, which corresponds to a yield of 71%.

In addition, the N-methylpyrrolidone mother liquor was diluted with four times the amount of 1:1 mixture of methanol and water to afford 11 g (yield 25%) of the 1:1 mixture of N,N'-bis(2,6-diisopropylphenyl)-1,6,8,11,16,18-hexa(p-tert-octylphenoxy)quaterrylene-3,4:13,14-tetracarboxylic diimide and N,N'-bis(2,6-diisopropylphenyl)-1,6,8,11,16,19-hexa(p-tert-octylphenoxy)quaterrylene-3,4:13,14-tetracarboxylic diimide of Example 6.

Example 11

38.7 g of the 1:1 mixture of N,N'-bis(2,6-diisopropyl-phenyl)-8,18-dibromo-1,6,11,16-tetra(p-tert-octylphenoxy)-quaterrylene-3,4:13,14-tetracarboxylic diimide and N,N'-bis(2,6-diisopropylphenyl)-8,19-dibromo-1,6,11,16-tetra(p-tert-octylphenoxy)quaterrylene-3,4:13,14-tetra-carboxylic diimide were reacted with 10.7 g of p-tert-octylphenol and 3.32 g of potassium carbonate in 170 ml of N-methyl-pyrrolidone similarly to Example 6, except that the reaction time was extended to 18 h.

This afforded 39.5 g of a 1:1 mixture of N,N'-bis(2,6-diiso-propylphenyl)-1,6,8,11,16,18-hexa(p-tert-octylphenoxy)-quaterrylene-3,4:13,14-tetracarboxylic diimide and N,N'-bis(2,6-diisopropylphenyl)-1,6,8,11,16,19-hexa(p-tert-octylphenoxy)quaterrylene-3,4:13,14-tetracarboxylic diimide in the form of a light green amorphous powder having a residual bromine content <0.05% by weight, which corresponds to a yield of 90%.

Example 12

The 1:1 mixture of N,N'-bis(2,6-diisopropylphenyl)-8,18-dibromo-1,6,11,16-tetra(p-tert-octylphenoxy)-quaterrylene-3,4:13,14-tetracarboxylic diimide and N,N'-bis(2,6-diiso-propylphenyl)-8,19-dibromo-1,6,11,16-tetra(p-tert-octylphenoxy)quaterrylene-3,4:13,14-tetra-carboxylic diimide of Example 10 (hereinafter designated "Ia") was converted by dehalogenation into N,N'-bis(2,6-diisopropy-lphenyl)-1,6,11,16-tetra(p-tert-octylphenoxy)quaterrylene-3,4:13,14-tetra-carboxylic diimide. The dehalogenation was conducted according to the following methods:

a) A mixture of 38.7 g of Ia and 600 ml of N-methylpyr-rolidone was stirred under nitrogen and heated to 130° C., admixed with 6.75 g of potassium tert-butoxide and maintained at 130° C. for 1.5 h.

After cooling down to room temperature, the reaction product was precipitated by adding the reaction mixture to 2l of 5% by weight hydrochloric acid, filtered off, washed first with 5% by weight hydrochloric acid to colorless run-off and then with water to neutral run-off and dried at 100° C. under reduced pressure. The isolated reaction product was then subjected to column chromatography over silica gel using 1:1 toluene/hexane as mobile phase.

This afforded 20.0 g of N,N'-bis(2,6-diisopropyl-phenyl)-1,6,11,16-tetra(p-tert-octylphenoxy)-quaterrylene-3,4:13, 14-tetracarboxylic diimide in the form of a light green amorphous powder having a UV/VIS spectroscopic purity of >99% and a residual bromine content <0.01%, which corresponds to a yield of 56%.

b) Example 12a) was repeated, except that 4.1 g of potassium carbonate was used as base instead of potassium tert-butoxide. The workup and purification were likewise carried out similarly to Example 12a).

This afforded 18.6 g of N,N'-bis(2,6-diisopropylphenyl)-1,6,11,16-tetra(p-tert-octylphenoxy)quaterrylene-3,4:13,14-tetracarboxylic diimide in the form of a light green amorphous powder having a purity of >99.5% and a residual bromine content of 0.00%, which corresponds to a yield of 52%.

c) A mixture of 38.7 g of Ia, 3.8 g of sodium borohydride, 0.46 g of tetrakis(triphenylphosphine)palladium(0) and 600 ml of dioxane was heated to 60° C. for 48 h while stirring in a nitrogen atmosphere.

After cooling down to room temperature, excess hydride was decomposed by gradual addition of 10 ml of water. The rest of the workup and purification was carried out similarly to Example 12a).

This afforded 21.7 g of N,N'-bis(2,6-diisopropyl-phenyl)-1,6,11,16-tetra(p-tert-octylphenoxy)-quaterrylene-3,4:13,14-tetracarboxylic diimide in the form of a light green amorphous powder having a purity of >99% and a residual bromine content of 0.00%, which corresponds to a yield of 61%.

d) A mixture of 38.7 g of Ia, 3.8 g of sodium borohydride, 0.23 g of tetrakis(triphenylphosphine)palladium(0) and 1000 ml of acetonitrile was heated to 69° C. for 25 h while stirring in a nitrogen atmosphere.

After cooling down to room temperature, excess hydride was decomposed by gradual addition of 10 ml of water. The rest of the workup and purification was carried out similarly to Example 12a).

This afforded 29.1 g of N,N'-bis(2,6-diisopropyl-phenyl)-1,6,11,16-tetra(p-tert-octylphenoxy)quaterrylene-3,4:13,14-tetracarboxylic diimide in the form of a light green amorphous powder having a purity of >99% and a residual bromine content of 0.00%, which corresponds to a yield of 82%.

Example 13 a) A mixture of 20.85 g (25 mmol) of N,N'-bis(2,6-diisopropyl-phenyl)terrylene-3,4:11,12-tetracarboxylic diimide, 20 g (125 mmol) of bromine and 1250 ml of chloroform was refluxed for 12 h in the dark with stirring. The reaction solution was cooled down to room temperature, the solvent was stripped off under reduced pressure, and the crude product was chromatographed over silica gel using dichloromethane as mobile phase.

This afforded 22.5 g of N,N'-bis(2,6-diisopropylphenyl)-1,6,9,14-tetrabromoterrylene-3,4:11,12-tetracarboxylic diimide in the form of a blue crystalline solid having a melting point >300° C., which corresponds to a yield of 78%.

Analytical data:

elemental analysis (% by weight, calculated/observed): C: 60.55/60.7, H: 3.7/3.7, N: 2.45/2.45, O: 5.55/5.6, Br: 27.75/27.55, mass (FD, 8 kV): m/z=1145.3 (M$^+$, 100%), IR (KBr): ν=1703 (s, C=O), 1660 (s, C=O) cm$^{-1}$, UV/VIS (CHCl$_3$): λ$_{max}$ (ε)=559 (15850), 605 (46770), 656 (93330) nm.

b) A mixture of 11.5 g (10 mmol) of N,N'-bis(2,6-diisopropyl-phenyl)-1,6,9,14-tetrabromoterrylene-3,4:11,12-tetra-carboxylic diimide, 10.3 g (50 mmol) of p-tert-octylphenol, 3.45 g (25 mmol) of potassium carbonate and 250 ml of N-methylpyrrolidone was heated to 80° C. under nitrogen for 8 h with stirring. The reaction mixture was cooled down to room temperature and diluted with three times the volume of 5% by weight hydrochloric acid, and the precipitated reaction product was filtered off, washed neutral with water, dried and subjected to column filtration over silica gel using methylene chloride as mobile phase.

This afforded 13.2 g of N,N'-bis(2,6-diisopropylphenyl)-1,6,9,14-tetra(p-tert-octylphenoxy)terrylene-3,4:11,12-tetra-carboxylic diimide in the form of a dark blue crystalline solid having a melting point >300° C., which corresponds to a yield of 80%.

Analytical data: elemental analysis (% by weight, calculated/observed): C: 82.85/82.8, H: 7.7/7.7, N: 1.7/1.7, O: 7.75/7.8, mass (FD, 8 kv): m/z=1651.2 (M$^+$, 100%), IR (KBr): ν=1708 (s, C=O), 1668 (s, C=O) cm$^{-1}$, UV/VIS (CHCl$_3$): λ$_{max}$ (ε)=628 (52930), 669 (128770) nm.

Example 14 a) Example 13a) was repeated, except that a mixture of 18.9 g (25 mmol) of N-cyclohexyl-N'-(2,6-diisopropylphenyl)-terrylene-3,4:11,12-tetracarboxylic diimide, 20 g (125 mmol) of bromine and 1250 ml of chloroform was used.

This afforded 19.8 g of N-cyclohexyl-N'-(2,6-diisopropylphenyl)-1,6,9,14-tetrabromoterrylene-3,4:11,12-tetra-carboxylic diimide in the form of a blue microcrystalline solid having a melting point >300° C., which corresponds to a yield of 74%.

Analytical data:

elemental analysis (% by weight, calculated/observed): C: 58.25/58.35, H: 3.4/3.4, N: 2.6/2.6, O: 5.95/6.0, Br: 29.8/29.65, mass (FD, 8 kV): m/z=1073.0 (M$^+$, 100%), IR (KBr): ν=1705 (s, C=O), 1662 (s, C=O) cm$^{-1}$, UV/VIS (CHCl$_3$): λ$_{max}$ (ε)=556 (16790), 600 (48290), 652 (90070) nm.

b) Example 13b) was repeated, except that a mixture of 10.7 g (10 mmol) of N-cyclohexyl-N'-(2,6-diisopropylphenyl)-1,6,9,14-tetrabromoterrylene-3,4:11,12-tetracarboxylic diimide, 10.3 g (50 mmol) of p-tert-octylphenol, 3.45 g (25 mmol) of potassium carbonate and 250 ml of N-methylpyrrolidone was used and the crude product was subjected to column filtration using dichloromethane.

This afforded 12.9 g of N-cyclohexyl-N'-(2,6-diisopropylphenyl)-1,6,9,14-tetra(p-tert-octylphenoxy)terrylene-3,4:11,12-tetracarboxylic diimide in the form of a dark blue crystalline solid having a melting point >300° C., which corresponds to a yield of 82%.

Analytical data:

elemental analysis (% by weight, calculated/observed): C: 85.9/85.8, H: 8.2/8.3, N: 1.8/1.8, O: 4.1/4.1, mass (FD, 8 kV): m/z=1565.3 (M$^+$, 100%), IR (KBr): ν=1709 (s, C=O), 1667 (s, C=O) cm$^{-1}$, UV/VIS (CHCl$_3$): λ$_{max}$ (ε)=624 (54010), 667 (129770) nm.

B) Evaluation and use of compounds I according to the invention

Example 15

The solubility of the compounds I prepared in Examples 1 to 14 was evaluated in extremely nonpolar to polar solvents. Generally, a distinctly improved solubility was observed compared to the compounds without tert-alkylphenoxy substitution. Details relating to these experiments are listed in Table 2.

The solubility of these compounds I was at least 10% by weight also in molten polystyrene, polymethyl methacrylate and polycarbonate.

TABLE 2

| Compound I of Ex. | Solubility [g/l] in | | |
|---|---|---|---|
| | Pentane (25° C.) | Toluene (25° C.) | Isopropanol (50° C.) |
| 1 | 53 | >250 | 56 |
| 2 | 81 | >400 | 92 |
| 3 | 65 | >350 | 87 |
| 4 | 55 | >250 | 59 |
| 5 | 24 | 155 | 47 |
| 6 | 55 | >500 | 49 |
| 7 | 55 | >500 | 49 |
| 8 | 12 | 88 | 10 |
| 12a | 51 | unlimited | 48 |
| 12b | 51 | unlimited | 48 |
| 12c | 51 | unlimited | 48 |
| 13b | 75 | unlimited | 56 |
| 14b | 72 | unlimited | 52 |

Example 16

Example 25 of WO-A-99/40123 was repeated to prepare aqueous polymer dispersions containing 15% by weight of the fluorescent colorant of Example 2 or 10/25% by weight of the near infrared absorber of Example 6 in homogeneous dispersion. The corresponding phenoxy-substituted derivatives, by contrast, were only incorporable with homogeneous results up to a concentration of respectively 7 and 1% by weight.

We claim:

1. A tert-alkyiphenoxy-substituted polycyclic compound of general formula I

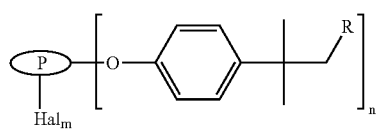

where

P is a conjugated polycyclic radical which is stable to bases and nucleophiles, optionally bears aryl substituents and contains no group from the group consisting of —CO—NH—CO—, —COOH and —CO—O—CO—, with the proviso that metal phthalocyanines and, if n is 4, N,N' disubstituted perylene-3,4:9,10-tetracarboxylic diimides shall be excluded, wherein the conjugated polycyclic radical is selected from the group consisting of naphthalenes, anthracenes, phenanthrenes, tetracenes, perylenes, terrylenes, quaterrylenes, pentarylenes, hexarylenes, anthraquinones, indanthrones, N-substituted naphthalene-1,8-dicarboxylic monoimides, N,N'-disubstituted naphthalene-1,8: 4,5-tetracarboxylic diimides, N-substituted perylene-3,4- dicarboxylic monoimides, N,N'-disubstituted perylene-3,4:9,10-tetracarboxylic diimides, N,N'-di-substituted terrylene-3,4:11,12-tetracarboxylic diimides, and N,N'-disubstituted quaterrylene-3,4:13,14-tetracarboxylic diimides;

R is $C_2$–$C_8$-alkyl, whose carbon chain may be interrupted by one or more groups selected from the group consisting of —O—, —S—, —NR$^1$—, —CO— and/or —SO$_2$— and which may be monosubstituted or polysubstituted by $C_1$–$C_6$-alkoxy or;

$C_5$–$C_8$-cycloalkyl whose carbon chain may be interrupted by one or more groups selected from the group consisting of —O—, —S—, —NR$^1$, —CO— and/or —SO$_2$— and which may be monosubstituted or polysubstituted by $C_1$–$C_6$-alkyl;

$R^1$ is hydrogen or $C_1$–$C_6$-alkyl;

Hal is chlorine and/or bromine;

m is from 0 to 15;

n is from 1 to 16, subject to the proviso that the sum m+n is 16.

2. A process for preparing a compound of general formula I as set forth in claim 1 comprising:

reacting a halide of general formula II

in an inert basic nitrogen-containing solvent in the presence of a base with a tert-alkylphenol of general formula III

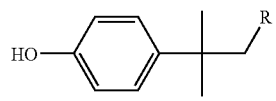

and optionally subsequently removing unwanted halogen.

3. A method of coloring a high molecular weight organic and/or inorganic material comprising:

mixing a high molecular weight organic and/or inorganic material with at least one compound of general formula I as set forth in claim 1.

4. A process for preparing a compound of general formula I as set forth in claim 1 comprising:

reacting a halide of general formula II

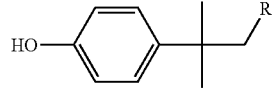

in an inert basic nitrogen-containing solvent in the presence of a base with a tert-alkyiphenol of general formula III

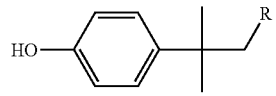

and optionally subsequently removing unwanted halogen.

5. A method of coloring a high molecular weight organic and/or inorganic material comprising:

mixing a high molecular weight organic and/or inorganic material with at least one compound of general formula I as set forth in claim 1.

6. An organic pigment comprising a dispersing aid and/or additive, wherein the dispersing aid and/or additive comprises a compound of general formula I as set forth in claim 1.

* * * * *